United States Patent

Roger et al.

[11] Patent Number: 5,935,173
[45] Date of Patent: Aug. 10, 1999

[54] KNEE PROSTHESIS

[75] Inventors: Gregory James Roger; Mervin John Cross, both of Crows Nest, Australia

[73] Assignees: Cryptych PTY LTD; MJ Cross PTY LTD, both of Crows Nest, Australia

[21] Appl. No.: 08/875,743
[22] PCT Filed: Feb. 5, 1996
[86] PCT No.: PCT/AU96/00054
  § 371 Date: Aug. 4, 1997
  § 102(e) Date: Aug. 4, 1997
[87] PCT Pub. No.: WO96/23458
  PCT Pub. Date: Aug. 8, 1996

[30] Foreign Application Priority Data

Feb. 3, 1995 [AU] Australia .................. PN0894

[51] Int. Cl.[6] .................................................. A61F 2/38
[52] U.S. Cl. ............................................................ 623/20
[58] Field of Search .................... 623/20, 23, 18

[56] References Cited

U.S. PATENT DOCUMENTS

| | | |
|---|---|---|
| 4,085,466 | 4/1978 | Goodfellow et al. . |
| 4,728,332 | 3/1988 | Albrektsson . |
| 5,116,375 | 5/1992 | Hofmann . |
| 5,236,461 | 8/1993 | Forte ........................................ 623/20 |

FOREIGN PATENT DOCUMENTS

| | | |
|---|---|---|
| 0 346 183 | 12/1989 | European Pat. Off. . |
| 0 349 173 | 1/1990 | European Pat. Off. . |
| 0 497 079 | 8/1992 | European Pat. Off. . |
| 0 529 408 A1 | 3/1993 | European Pat. Off. ................. 623/20 |
| 0 546 726 | 6/1993 | European Pat. Off. . |
| 0 551 791 A1 | 7/1993 | European Pat. Off. ................. 623/20 |
| 0 582 514 | 2/1994 | European Pat. Off. . |
| 0 627 203 | 12/1994 | European Pat. Off. . |
| 0 636 353 A1 | 2/1995 | European Pat. Off. ................. 623/20 |
| 1 413 477 | 1/1972 | United Kingdom . |
| 1 485 681 | 1/1975 | United Kingdom . |
| 2 253 147 | 9/1992 | United Kingdom . |

*Primary Examiner*—David H. Willse
*Attorney, Agent, or Firm*—Jacobson, Price, Holman & Stern, PLLC

[57] ABSTRACT

A knee prosthesis of the meniscal knee type having at least a tibial component, a femoral component and a meniscal bearing to be placed between the tibial and femoral components. The bearing surface of the femoral component having a first anterior portion having a radius of curvature greater than the radius of curvature of a second posterior portion and the meniscal bearing having an upper surface having first and second bearing portions respectively substantially congruent with the first and second bearing portions of the femoral component. The first and second bearing surface of the meniscal bearing being separated by a short area which is planar or has a longer radius of curvature than either of the first and second bearing surface. The meniscal bearing has a heel extending posteriorly beyond the extend of the concave portion of its upper surface.

40 Claims, 4 Drawing Sheets

KNEE PROSTHESIS

FIELD OF THE INVENTION

The present invention relates to improvements in knee prostheses and in particular to knee prostheses of the type having a femoral component and a tibial component which each bear on an intervening meniscal bearing.

BACKGROUND ART

The normal human knee is capable of complex motion including flexion/extension, adduction/abduction, anterior femoral-tibial shift, and axial rotation. Successful knee replacement with a prosthesis requires that the bearing surfaces achieve two roles which are contradictory in their physical application.

The first role is that the bearing surfaces and their geometries allow the knee a natural range of movement as determined by the ligaments and soft tissue surrounding the knee. This movement includes flexion/extension, roll back of femur on the tibia and finally rotation of the femur on the tibia at all angles of flexion.

The second role is that the transmission of weight and the friction of movement do not degrade the bearing materials over a reasonable period of time. The aim is that the prosthesis will outlast the patient. To achieve low contact stresses between the bearing surfaces implies a high contact area between those surfaces, ie. a high degree of component congruency. This, in turn, means that there must be a degree of constriction in movement between the bearing surfaces which contradicts the first role mentioned above.

The best solution to date has been the "meniscal knee" developed by Goodfellow and O'Connor in Oxford, England (see U.S. Pat. No. 4,085,466) in 1972. This knee provides a three part articulation comprising a curved femoral surface, a flat tibial surface and a meniscal bearing between the femoral and tibial surfaces. The meniscal bearing is normally formed of a suitable synthetic plastics material such as ultra high molecular weight polyethylene. It has a flat lower surface that slides on the tibial surface and a concave upper surface that receives the femoral surface. Constraint, and the shear stresses that go with it, is generally avoided as the meniscal bearing slides about on the flat tibial surface as the knee flexes, rolls and rotates.

While development of the meniscal knee has been well received there are a number of difficulties still inherent in prostheses of this type. The surgical placement of such prostheses has to be very precise and technical failure for this reason is common. There is also a tendency for the meniscal bearing to dislocate, or spit out, in flexion as the forces applied may be very high.

Other knee prostheses have been developed in which the sliding meniscus is restrained or guided in some way. One variant has curved rails which entrap and guide two sliding menisci, one for each side of the knee joint. A problem with these further variants is that sheer stress transmission, while reduced, is still present and dislocation of the menisci can still occur. Further, when rails are utilised, the result is a highly constrained knee except in the exact geometry of the rails.

DISCLOSURE OF THE INVENTION

The present invention is directed to improvements to knee prosthesis of the "meniscal knee" type that are intended, in preferred embodiments at least to increase the area of weight transmission through the meniscal bearing to the tibial plateau. This increase in contact area is designed to be achieved without constraining the natural sliding and rotation of the knee during flexion and extension, and without leading to the increased transmission of shear forces from the femur to the tibia.

In a first aspect the present invention consists in a knee prosthesis comprising a tibial component, a femoral component and a meniscal bearing the tibial component being adapted for connection to the tibia of a patient and to provide a substantially planar resurfacing of the tibial plateau, the femoral component being adapted for connection to the femur of the patient and to provide a bearing surface having a first, anterior, bearing portion having a first radius of curvature in an anterior-posterior plane, and at least a second, posterior, bearing portion having a second radius of curvature in that plane which is smaller than the first radius, and the meniscal bearing being adapted to be placed between the tibial and femoral components, the meniscal bearing having a substantially planar lower surface adapted for sliding movement over the surface of the tibial component, and the meniscal bearing having an upper surface which is concave when seen along the anterior-posterior plane and having a first, anterior, bearing surface substantially congruent with the first bearing portion of the femoral component and a second, posterior, bearing surface substantially congruent with the second bearing portion of the femoral component, the first and second bearing surfaces of the meniscal bearing being separated by a short area between them which is planar or of longer radius of curvature than either of the first and second bearing surfaces in the anterior-posterior plane.

In a further aspect the present invention consists in a knee prosthesis comprising a tibial component, a femoral component and a meniscal bearing, the tibial component being adapted for connection to the tibia of a patient and to provide a substantially planar resurfacing of the tibial plateau, the femoral component being adapted for connection to the femur and having an arcuate bearing surface, the meniscal bearing being adapted to be placed between the tibial and femoral components, the meniscal bearing having a substantially planar lower surface adapted for sliding movement over the surface of the tibial component and an upper surface having a concave portion adapted to receive the arcuate bearing surface of the femoral component, the knee prosthesis being characterised in that the meniscal bearing extends posteriorly beyond the extent of the concave portion of the upper surface.

The present inventors believe that the reason high conformity between the femoral surface and the upper surface of the meniscal bearing causes meniscal dislocation or failure is that as the femur rolls back, during flexion, it pushes on the posterior part of the meniscal bearing. This pressure on the posterior part of the meniscal bearing will tend to tilt its anterior end upwardly. Also, as the part of the femur contacting the meniscal bearing at full flexion is of a smaller radius than most meniscal bearings, the femur tends to roll over the posterior edge of the meniscal bearing, which may then dislocate anteriorly.

With reference to the first aspect of the invention it is preferred that there is a high degree of congruency between the first bearing portion of the femoral component and the first bearing surface of the meniscal bearing and between the second bearing portion of the femoral component and the second bearing surface of the meniscal bearing. The first and second bearing surfaces of the meniscal bearing are separated in the anterior-posterior plane by a planar area or an area of a radius greater than the radius of the first bearing portion of the femoral component. The separation between the two bearing surfaces is preferably as small as possible while still allowing clearance of the first radius of curvature of the femur from the posterior part of the meniscus at full extension.

The separation is preferably from 1 to 4 mm, more preferably 0.5 to 2.5 mm, and most preferably 1 to 2 mm.

With reference to the second aspect of the invention the extension of meniscal bearing posteriorly of the extent of the concave surface on the upper side provides a posteriorly extending "heel" on the meniscal bearing. This "heel" resists any tendency of the meniscal bearing to be tilted upwardly when the knee is fully flexed. The heel can extend posteriorly substantially horizontally beyond the extent of the concave portion of the upper surface. The planar lower surface preferably extends exteriorly beyond the extent of the upper surface. The upper surface of the meniscal bearing further preferably slopes smoothly down from the posterior edge of the concave portion to the posterior edge of the planar lower surface of the meniscal bearing.

It is preferred that the tibial component comprises a plate. The plate is preferably planar. The tibial component can also have at least its upper surface comprised of polished chromium alloy. The plate is preferably formed on its underside with fixation means such as pegs or screws adapted for insertion into undersized holes formed in the tibial plateau. The pegs serve to hold the tibial component in place on the tibia. If desired other means for engagement of the tibial component with the tibia could be used. While it is strongly preferred that the upper surface of the tibial component is planar it could be formed with grooves in a known manner to receive corresponding ribs formed on the underside of the meniscal bearing.

The meniscal bearing is preferably formed of a high density synthetic plastics material such as ultra high molecular weight polyethylene (UHMWPE). In order to avoid exceeding the yield stress in the meniscal bearing it is preferred that when it is formed of UHMWPE it has a thickness of at least 6 mm. If formed of other materials corresponding minimum thicknesses may be calculated. The meniscal bearing is preferably horseshoe shaped having a recess in its posterior surface to allow the passage therethrough of the patient's posterior cruciate ligament. If intact the patient's anterior cruciate ligament will normally be sacrificed. Alternatively, the recess in the meniscal bearing may be replicated anteriorly to receive both the anterior and posterior cruciate ligament. Alternatively the meniscal bearing may be in two parts, medial or lateral, so that the central cruciate insertion areas are avoided.

The normal femur includes a pair of femoral condyles separated by the trochlear groove. Similarly the femoral component preferably includes a pair of condylar surfaces each of which has the shape defined above in an anterior/posterior plane. The upper surface of the meniscal bearing is most preferably formed with a pair of grooves each adapted to receive one of the condylar surfaces of the femoral component. These grooves are preferably each formed to substantially conform to the anterior/posterior curvature of the condylar surfaces with the exception of the space between the first and second bearing portions. When seen in a medio-lateral plane the condylar surfaces, and the corresponding surfaces of the grooves in the meniscal bearing, are preferably constant and substantially congruent along their length. The femoral component preferably has at least its bearing surface comprised of a chromium alloy.

The first bearing surface can comprise the surface of an anterior flange of the femoral component which preferably is also adapted to articulate with a patellar or patellar component. The patellar component is adapted to be attached to the posterior side of the patellar. It preferably has a bearing surface that slidingly engages congruently with the femoral component. As the knee is flexed the patellar component will move into contact with the trochlear groove. It is preferably formed at its lateral ends with facets that conform to the curvature of the condylar surfaces on each side of the trochlear groove.

BEST METHOD OF CARRYING OUT THE INVENTION

An embodiment of a knee prosthesis according to the present invention is generally depicted as 10 in the Figures.

The knee prosthesis 10 comprises a femoral component 11, a tibial component 12 and between them a meniscal bearing 13.

Figure 3:
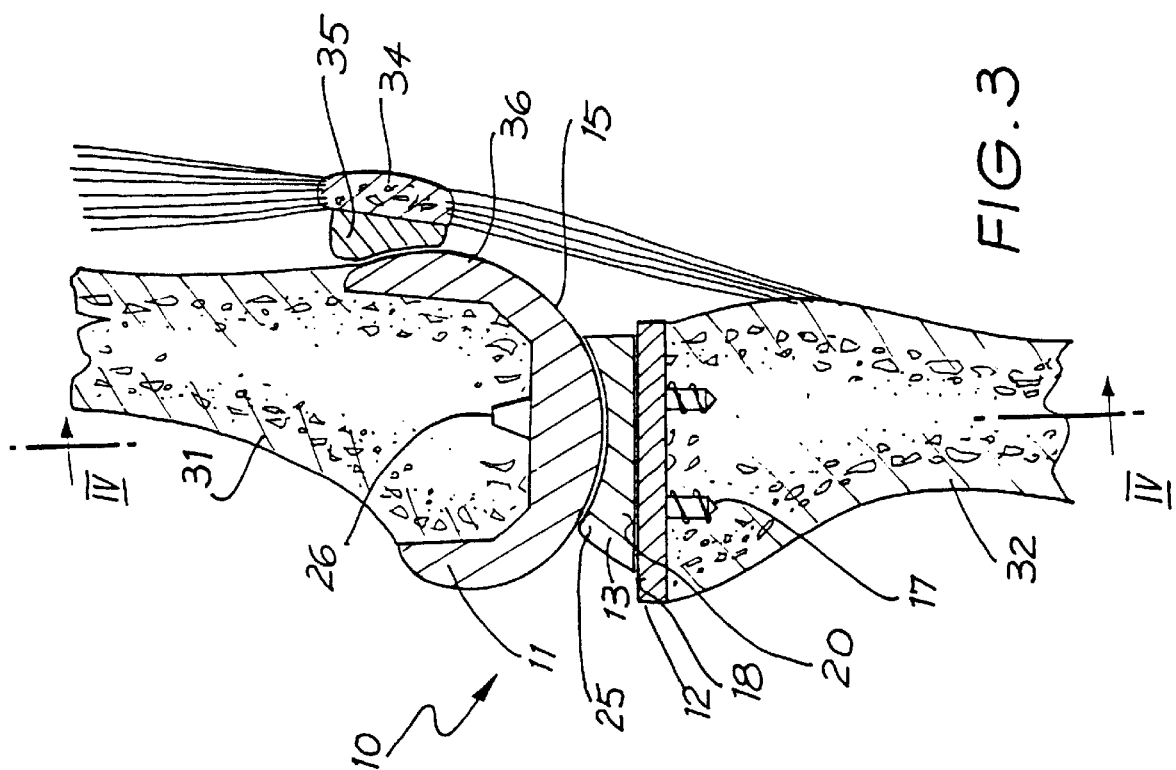
FIG. 3 is a section in an anterior-posterior plane through a second embodiment of a knee prosthesis according to the present invention, with the patellar and patellar component present as shown.

The femoral component 11 is formed of a suitable chromium alloy and is adapted to be attached to the distal end of the femur 31 (see FIG. 3). The femoral component 11 comprises an anterior flange 36 and a pair of substantially parallel condylar bearing surfaces 14 and 15. Each of the condylar bearing surfaces 14 and 15 has at least a first radius R1 (see FIG. 1) in the anterior-posterior plane, at an anterior location, and a smaller second radius R2 at a posterior location. The second radius R2 represents the bearing surface that bears against the meniscal bearing 13 when the knee is flexed by about 40° or more. As seen in FIG. 3, the anterior flange 36 is adapted to slidingly engage with a patellar component 35 which is attached to the posterior side of the patellar 34. As the knee 10 is flexed, the patellar component 35 will move into contact with the trochlear groove 37 that separates the femoral condyles 38 and 39.

The tibial component 12 comprises a flat plate 16 having a pair of downwardly extending pins 17 on its underside to allow attachment of the component 12 to the proximal end of the tibia 32 (see FIG. 3). The upper surface 18 of the tibial component 12 is flat and smooth. The tibial component 12 is also formed of a suitable chromium alloy.

The meniscal bearing 13 is formed of an ultra high molecular weight polyethylene. The meniscal bearing 13 is U-shaped in this embodiment (see FIG. 5) with the base of the U 33 being directed anteriorly. The cut-out 19 in the U-shaped meniscal bearing 13 (see FIG. 5) provides space for the posterior cruciate ligament if it is retained. If it is desired to accommodate both the anterior and posterior cruciate ligaments the cut-out 19 would need to be deeper, or the bearing to be in two sections (see FIG. 6).

The underside 20 of the meniscal bearing 13 is flat and smooth. It is adapted to slide smoothly over the upper surface 18 of the tibial component 12. The upper side of the meniscal bearing 13 is provided with a pair of recesses 21. Each recess is adapted to receive one of the condylar bearing surfaces 14 and 15 of the femoral component. In a medio-lateral plane the recesses 21 are arcuate and correspond in shape with the substantially uniform shape of the condylar bearing surfaces 14 and 15 when sectioned medio-laterally. In an anterior-posterior plane each of the recesses 21 has a first, anterior, section 22 having the radius R1 and a second, posterior, section 23 having the radius R2. These sections are spaced apart by a substantially planar section 24 which is about 2 mm wide. While sections 22 and 23 are separated by a planar section 24 in the depicted embodiment, the section 24 can comprise a portion having a longer radius of curvature than R1 and R2. The presence of the planar section 24 between the section 22 and 23 allows the condylar bearing surfaces 14 and 15 to each be substantially congruent with a portion of the surface of one of the recesses 21 throughout the full range of flexion and extension of the knee. The presence of this planar section 24 means that this congruency is not at the expense of the femur abutting on the posterior edge of the meniscal bearing 13 which would tend to tilt its anterior edge 33 upwardly, or cause high wear. It is believed that such action would contribute to the possibility of the meniscal bearing 13 being ejected from between the tibial and femoral components of prior art arrangements.

Figure 1:
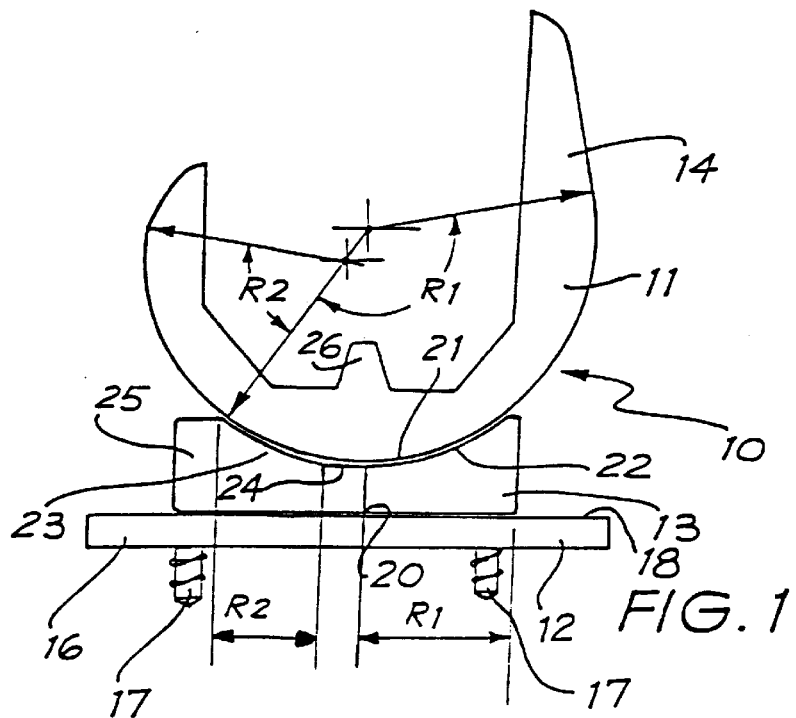
FIG. 1 is a diagrammatic anterior-posterior sectional view through a first embodiment of a knee prosthesis according to the present invention.
Figure 2:
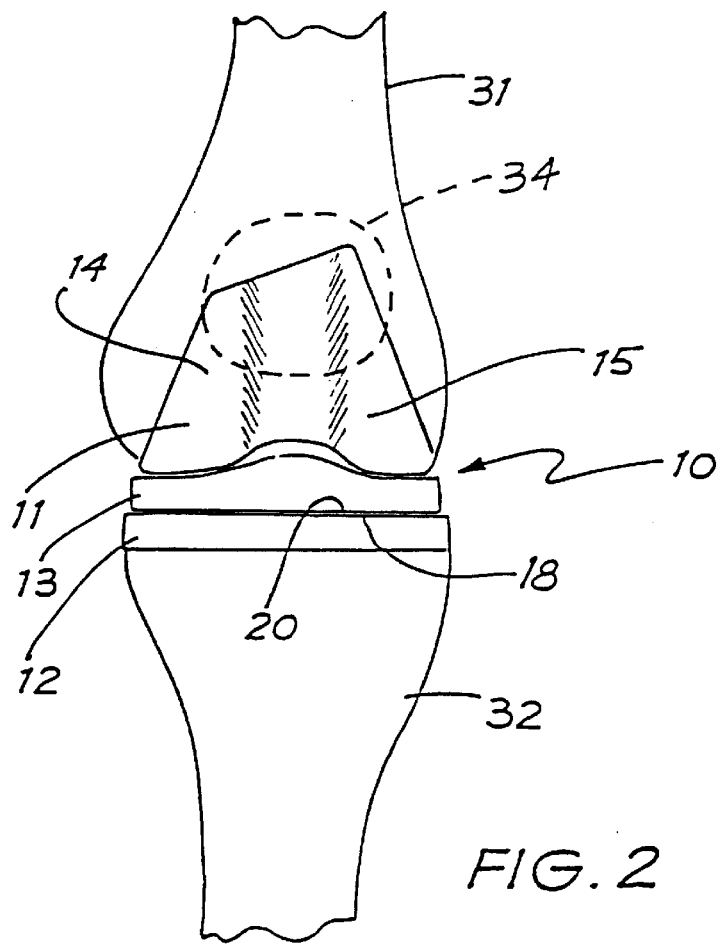
FIG. 2 is an anterior view of the knee prosthesis according to FIG. 1 in place but with the patellar and the patellar component of the prosthesis removed for clarity, the position of the patellar being shown in broken lines.
Figure 4:
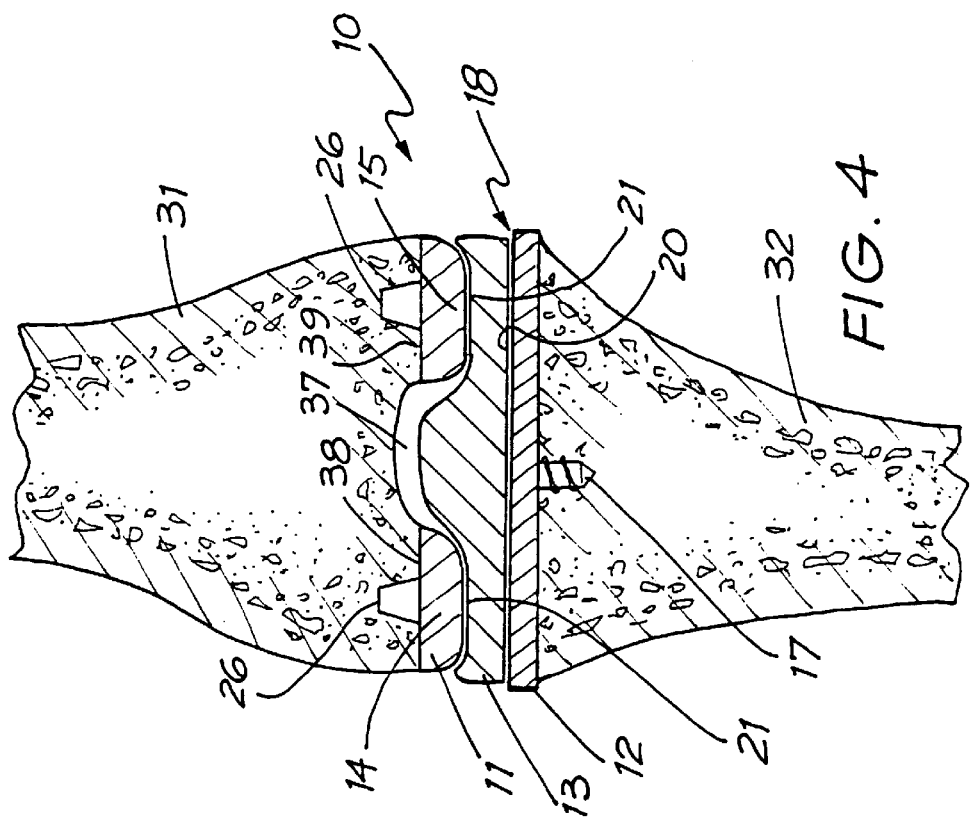
FIG. 4 is a section in a media-lateral plane through the prosthesis of FIG. 3 along line IV—IV of FIG. 3.
Figure 5:
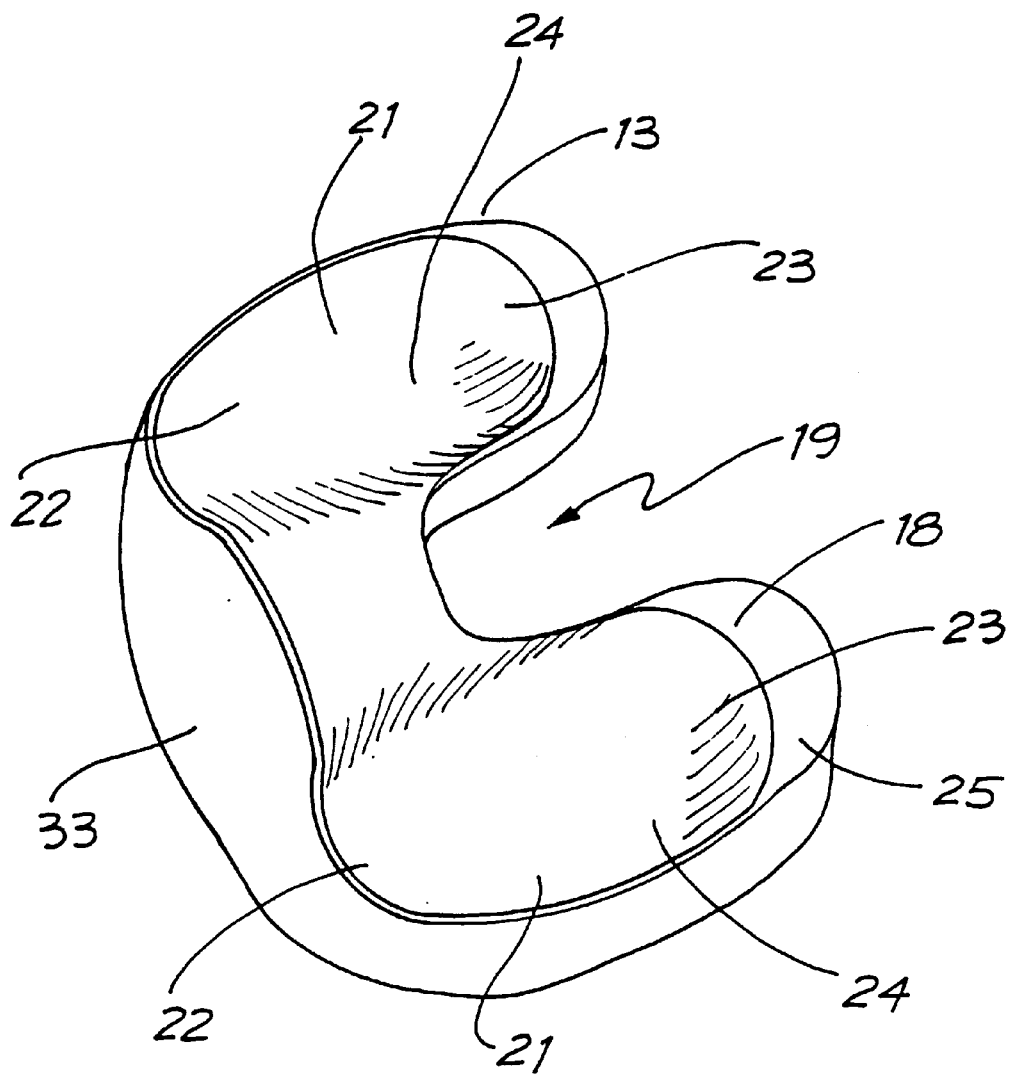
FIG. 5 is a perspective view of the meniscal bearing of FIG. 1 for use in a prosthesis according to the present invention.
Figure 6:
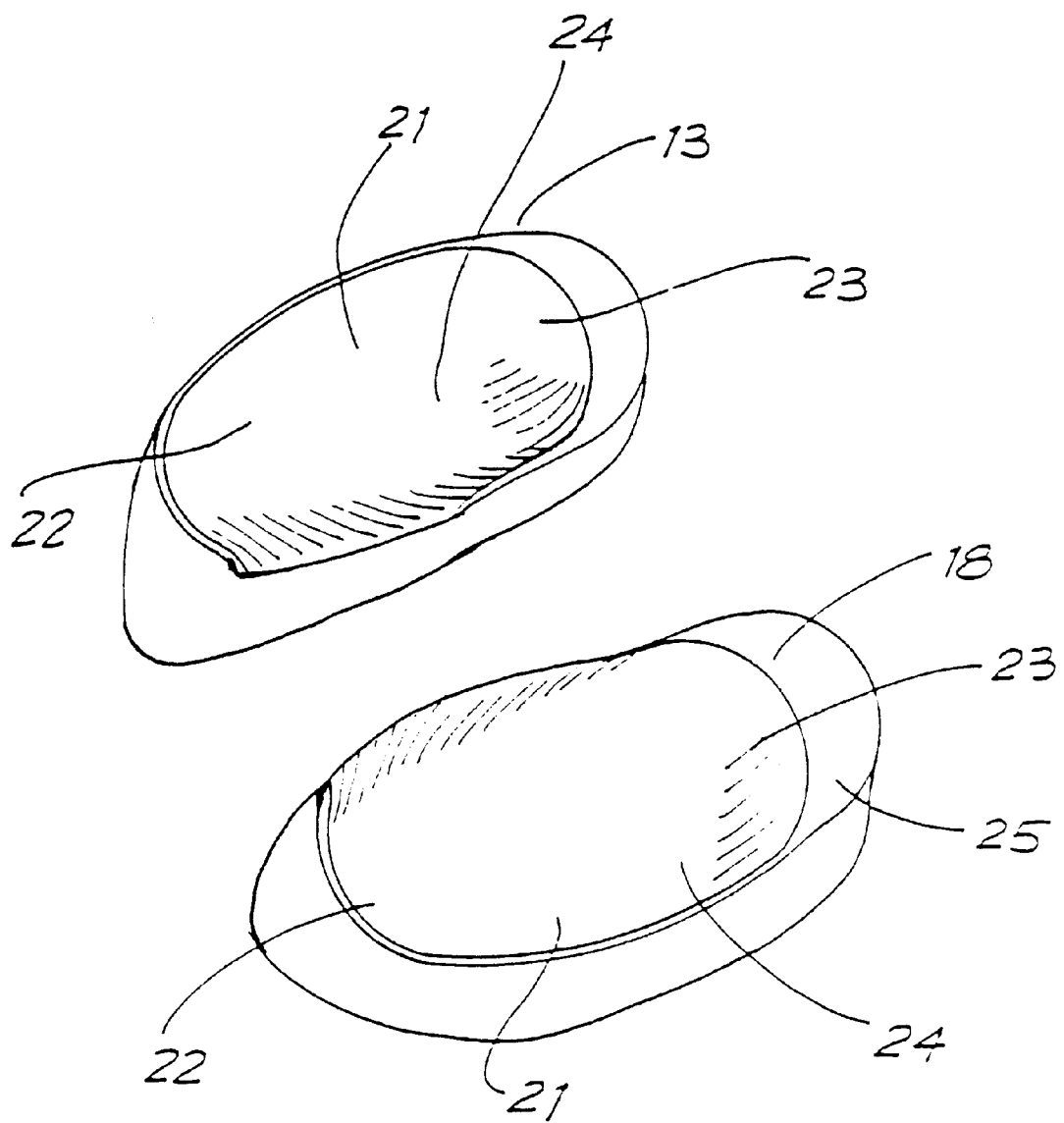
FIG. 6 is a perspective view of a second embodiment of a meniscal bearing for use in a prosthesis according to the present invention.

The meniscal component 13 extends posteriorly beyond each of the recesses 21 to provide a "heel" 25 to the meniscal component 13. The heel may extend posteriorly substantially horizontally from the back of each recess 21 as is seen in FIGS. 1 and 5. Alternatively, the heel may slope downwardly from the back of each recess 21 to meet the underside 20 as is seen in the embodiment depicted in FIG. 3. In either case the heel 25 prevents the meniscal bearing 13 from lifting at its anterior edge 33 when the knee is in full flexion.

The knee prosthesis 10 may be inserted using known surgical techniques such as those generally described in U.S. Pat. No. 4,340,978 the contents whereof are incorporated herein by reference. The femoral component 11 and the tibial component 12 are held in place respectively by a pair of pins 26 and by the pins 17 together with a bone cement such as polymethyl methacrylate or known methods of cement-free fixation.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A knee prosthesis comprising a tibial component, a femoral component and a meniscal bearing, the tibial component being connectable to the tibia of a patient and having a substantially planar surface that provides a resurfacing of the tibial plateau, the femoral component being connectable to the femur of the patient and having a bearing surface having a first, anterior, bearing portion having a first radius of curvature in an anterior-posterior plane, and at least a second, posterior, bearing portion having a second radius of curvature in that plane which is smaller than the first radius, and the meniscal bearing being placed between the substantially planar surface of the tibial component and the bearing surface of the femoral component and having a substantially planar lower surface to enable unconstrained slidable movement relative to the substantially planar surface of the tibial component in all directions along the plane, the meniscal bearing further having an upper surface which is concave when seen along the anterior-posterior plane and having a first, anterior, bearing surface substantially congruent with the first bearing portion of the femoral component and a second, posterior, bearing surface substantially congruent with the second bearing portion of the femoral component, the first and second bearing surfaces of the meniscal bearing being separated by a short area between them which is planar or of longer radius of curvature than either of the first and second bearing surfaces in the anterior-posterior plane.

2. The knee prosthesis of claim 1 wherein there is a high degree of congruency between the first bearing portion of the femoral component and the first bearing surface of the meniscal bearing and between the second bearing portion of the femoral component and the second bearing surface of the meniscal bearing.

3. The knee prosthesis of claim 1 wherein the separation between the first and second bearing surfaces is about 2 mm.

4. The knee prosthesis of claim 1 wherein the tibial component comprises a plate.

5. The knee prosthesis of claim 4 wherein the plate is planar.

6. The knee prosthesis of claim 4 wherein the plate is formed on its underside with fixation means for affixing the plate to a proximal end of a tibia.

7. The knee prosthesis of claim 6 wherein the fixation means comprises at least one peg or screw.

8. The knee prosthesis of claim 1 wherein the tibial component has at least its upper surface comprised of polished chromium alloy.

9. The knee prosthesis of claim 1 wherein the meniscal bearing is formed of a high density synthetic plastics material.

10. The knee prosthesis of claim 9 wherein the high density plastics material is ultra high molecular weight polyethylene (UHMWPE).

11. The knee prosthesis of claim 10 wherein the meniscal bearing has a thickness of at least 6 mm.

12. The knee prosthesis of claim 1 wherein the meniscal bearing is horseshoe shaped having a recess in its posterior surface to allow passage therethrough of a posterior cruciate ligament.

13. The knee prosthesis of claim 1 wherein the meniscal bearing has a recess in both its anterior surface and posterior surface to allow, respectively, passage therethrough of an anterior and posterior cruciate ligament.

14. The knee prosthesis of claim 1 wherein the meniscal bearing is formed in two parts so that the central cruciate insertion areas are avoided.

15. The knee prosthesis of claim 1 wherein the femoral component includes a pair of condylar surfaces each having an anterior/posterior curvature to allow fixation of the femoral component to a distal end of a femur.

16. The knee prosthesis of claim 15 wherein the upper surface of the meniscal bearing is formed with a pair of grooves each adapted to receive one of the condylar surfaces of the femoral component.

17. The knee prosthesis of claim 16 wherein the grooves are formed to substantially conform to the anterior/posterior curvature of the condylar surfaces with the exception of the short area between the first and second bearing surfaces.

18. The knee prosthesis of claim 1 wherein the femoral component has at least its bearing surface comprised of a chromium alloy.

19. The knee prosthesis of claim 1 wherein the first, anterior, bearing portion comprises the surface of an anterior flange of the femoral component.

20. The knee prosthesis of claim 19 wherein the anterior flange is adapted to articulate with a patella or patellar component.

21. The knee prosthesis of claim 20 wherein the patellar component is adapted to be attached to the posterior side of the patella and has a bearing surface that slidingly engages congruently with the femoral component.

22. A knee prosthesis comprising a tibial component, a femoral component and a meniscal bearing, the tibial component being connectable to the tibia of a patient and having a substantially planar surface that provides a resurfacing of the tibial plateau, the femoral component being connectable to the femur and having an arcuate bearing surface, the meniscal bearing being placed between the substantially planar surface of the tibial component and the arcuate bearing surface of the femoral component and having a substantially planar lower surface to enable unconstrained slidable movement relative to the substantially planar surface of the tibial component in all directions along the plane, the meniscal bearing further having an upper surface having a concave portion that receives the arcuate bearing surface of the femoral component and a portion that extends posteriorly beyond the extent of the concave portion of the upper surface.

23. The knee prosthesis of claim 22 wherein the meniscal bearing extends posteriorly substantially horizontally beyond the extent of the concave portion of the upper surface.

24. The knee prosthesis of claim 22 wherein the lower surface extends exteriorly beyond the extent of the upper surface.

25. The knee prosthesis of claim 24 wherein the upper surface of the meniscal bearing slopes smoothly down from a posterior edge of the concave portion to a posterior edge of the planar lower surface of the meniscal bearing.

26. The knee prosthesis of claim 22 wherein the tibial component comprises a plate.

27. The knee prosthesis of claim 26 wherein the plate is planar.

28. The knee prosthesis of claim 26 wherein the plate is formed on its underside with fixation means for affixing the plate to a proximal end of a tibia.

29. The knee prosthesis of claim 28 wherein the fixation means comprises at least one peg or screw.

30. The knee prosthesis of claim 22 wherein the tibial component has at least its upper surface comprised of polished chromium alloy.

31. The knee prosthesis of claim 22 wherein the meniscal bearing is formed of a high density synthetic plastics material.

32. The knee prosthesis of claim 31 wherein the high density synthetic plastics material is ultra high molecular weight polyethylene (UHMWPE).

33. The knee prosthesis of claim 32 wherein the meniscal bearing has a thickness of at least 6 mm.

34. The knee prosthesis of claim 22 wherein the meniscal bearing is horseshoe shaped having a recess in a posterior surface thereof to allow passage therethrough of a posterior cruciate ligament.

35. The knee prosthesis of claim 22 wherein the meniscal bearing has a recess in anterior and posterior surfaces thereof to allow, respectively, passage therethrough of an anterior and posterior cruciate ligament.

36. The knee prosthesis of claim 22 wherein the meniscal bearing is formed in two parts so that the central cruciate insertion areas are avoided.

37. The knee prosthesis of claim 22 wherein the femoral component includes a pair of condylar surfaces having an anterior/posterior curvature to allow fixation of the femoral component to a distal end of a femur.

38. The knee prosthesis of claim 37 wherein the upper surface of the meniscal bearing is formed with a pair of grooves each adapted to receive one of the condylar surfaces of the femoral component.

39. The knee prosthesis of claim 22 wherein the arcuate bearing surface of the femoral component has a first, anterior, bearing portion having a first radius of curvature in an anterior-posterior plane, and at least a second, posterior, bearing portion having a second radius of curvature in that plane which is smaller than the first radius, the concave upper surface of the meniscal bearing having a first, anterior, bearing surface substantially congruent with the first bearing portion of the femoral component and a second, posterior, bearing surface substantially congruent with the second bearing portion of the femoral component, the first and second bearing surfaces of the meniscal bearing being separated by a short area between them which is planar or of longer radius of curvature than either of the first and second bearing surfaces in the anterior-posterior plane.

40. The knee prosthesis of claim 22 wherein the femoral component has at least its bearing surface comprised of a chromium alloy.

\* \* \* \* \*